United States Patent
Huang

(10) Patent No.: US 7,433,034 B1
(45) Date of Patent: Oct. 7, 2008

(54) DARKFIELD DEFECT INSPECTION WITH SPECTRAL CONTENTS

(75) Inventor: Chunsheng Huang, San Jose, CA (US)

(73) Assignee: Nanometrics Incorporated, Milpitas, CA (US)

( * ) Notice: Subject to any disclaimer, the term of this patent is extended or adjusted under 35 U.S.C. 154(b) by 242 days.

(21) Appl. No.: 11/156,073

(22) Filed: Jun. 17, 2005

(51) Int. Cl.
  *G01N 21/00* (2006.01)
(52) U.S. Cl. .................................. 356/237.5
(58) Field of Classification Search ................ 356/300, 356/364–369, 237.1–237.5, 239.1, 239.3, 356/239.7, 239.8
See application file for complete search history.

(56) References Cited

U.S. PATENT DOCUMENTS

| | | | | |
|---|---|---|---|---|
| 3,973,849 | A * | 8/1976 | Jackson et al. | 356/320 |
| 4,895,445 | A * | 1/1990 | Granger | 356/328 |
| 5,412,468 | A * | 5/1995 | Lundberg et al. | 356/326 |
| 5,798,829 | A | 8/1998 | Vaez-Iravani | 356/237 |
| 5,917,588 | A | 6/1999 | Addiego | 356/237 |
| 6,271,916 | B1 | 8/2001 | Marxer et al. | 356/237.3 |
| 6,515,745 | B2 * | 2/2003 | Vurens et al. | 356/369 |
| 6,538,730 | B2 | 3/2003 | Vaez-Iravani et al. | 356/237.2 |
| 6,633,831 | B2 | 10/2003 | Nikoonahad et al. | 702/155 |
| 6,772,084 | B2 * | 8/2004 | Bischoff et al. | 702/127 |
| 6,778,267 | B2 | 8/2004 | Drake | 356/237.1 |
| 6,781,688 | B2 | 8/2004 | Kren et al. | 356/237.4 |
| 6,816,249 | B2 | 11/2004 | Fairley et al. | 356/237.1 |
| 6,954,267 | B2 * | 10/2005 | Abraham et al. | 356/237.2 |
| 7,088,443 | B2 * | 8/2006 | Vaez-Iravani et al. | 356/237.2 |
| 2002/0182760 | A1 * | 12/2002 | Wack et al. | 438/14 |
| 2004/0183017 | A1 * | 9/2004 | Kamiya et al. | 250/311 |
| 2004/0246476 | A1 * | 12/2004 | Bevis et al. | 356/237.5 |
| 2006/0038984 | A9 * | 2/2006 | Vaez-Iravani et al. | 356/237.1 |

* cited by examiner

*Primary Examiner*—Tarifur R Chowdhury
*Assistant Examiner*—Jonathon D Cook
(74) *Attorney, Agent, or Firm*—Silicon Valley Patent Group LLP; Michael J. Halbert

(57) ABSTRACT

A metrology device produces broadband illumination, e.g., an illumination line, that is incident on a substrate at an oblique angle of incidence and which is scanned across the substrate. A first detector collects a darkfield image, while a second detector collects the spectrally reflected light. The angle of incidence of the illumination is variable so that the darkfield image is received by the first detector without interference from diffracting structures on the substrate. Alternatively, the position of the first detector may be varied to receive the darkfield image, or a filter may be used to filter out light from any non-defect diffracting structures on the substrate. A processor uses the darkfield data from the first detector to determine if a defect is present on the substrate and uses the spectral data from the second detector to identify the material composition of the defect.

32 Claims, 2 Drawing Sheets

DARKFIELD DEFECT INSPECTION WITH SPECTRAL CONTENTS

FIELD OF THE INVENTION

The present invention relates to detection of defects and, more particularly, to defect inspection and identification.

BACKGROUND

The fabrication of semiconductor devices, or similar types of devices, typically includes a number of processing steps to form desired features and multiple layers on a substrate. In general, the processing steps used to form semiconductor devices on a substrate are well known and includes processes such as deposition, etching, photolithography, and chemical mechanical polishing.

Due to the complexity and need for accuracy in semiconductor fabrication, monitoring and evaluation of the processing is often required. One type of necessary monitoring is defect inspection. Defects are sometimes introduced during processing and typically include contaminants, or other non-uniformities, and scratches. The presences of defects may result in malfunctioning devices and a reduction in the overall yield. Accordingly, defect inspection is used to identify chips with defects as well as to identify processing steps that are causing defects to prevent further defect generation in subsequent processing.

SUMMARY

In accordance with an embodiment of the present invention, a metrology device produces broadband illumination on a portion of a substrate at an oblique angle of incidence. In one embodiment, the illumination may be a line of illumination. A darkfield detector collects the darkfield image from the illumination, while another detector collects the spectrally reflected light from the illumination. In one embodiment, the angle of incidence of the illumination may be variable to reduce or eliminate interference with the darkfield image from any diffracting structures on the substrate. Alternatively, the darkfield detector may be variable to receive the darkfield image without interference, or a filter may be used to filter out any interference. A processor uses the data from the darkfield detector to determine if a defect is present on the substrate and uses the data from the detector in the spectral path to identify the material composition of the defect.

In another embodiment, a method of detecting and identifying the material composition of defects on a substrate includes producing broadband light illuminating a portion of the surface of a substrate at an oblique angle of incidence. In one embodiment, the broadband light is formed into a line of illumination on the surface of the substrate. The illumination is scanned across the surface of the substrate, e.g., by moving the substrate or the optics (or both), while the darkfield image is collected with a first detector and the spectrally reflected light is collected with a second detector. The presence of a defect on the surface of the substrate is determined using the collected darkfield image and the material composition of the defect is determined using the collected spectrally reflected light.

In another embodiment, an apparatus includes a stage for holding a substrate and a metrology device for detecting and identifying defects on the substrate on the stage. At least one of the stage and the metrology unit is movable with respect to the other to produce a relative movement between the substrate held on the stage and the metrology unit. The metrology unit includes a variable angle light source that produces a polychromatic beam of light that is incident on the substrate at an oblique angle and at least one optical element that produces an illumination line on the substrate held on the stage, the at least one optical element collimates the beam of light in a first direction and focuses the beam of light in a second direction that is orthogonal to the first direction. A variable angle detector collects the spectrally reflected light from the substrate. The detector includes an array of photo-detecting elements that collect the spectrum of the spectrally reflected light along a first dimension during the relative movement between the substrate and the metrology unit. Another detector collects a darkfield image from the illumination line on the substrate. The darkfield detector is an array of photodetecting elements that collects the darkfield image of the length of the illumination line during the relative movement between the substrate and the metrology unit.

DETAILED DESCRIPTION

Figure 1:
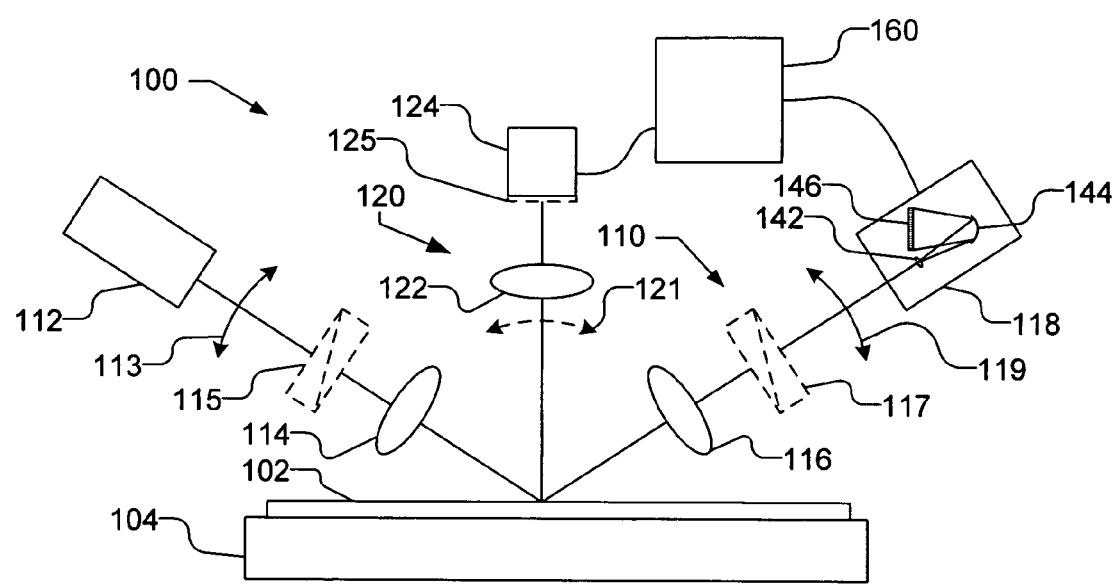
FIG. 1 is a schematic view of a metrology device that uses darkfield defect inspection along with spectrometry to detect defects as well as identify the material composition of the defect, in accordance with an embodiment of the present invention.

FIG. 1 is a schematic view of a metrology device 100 that uses darkfield defect inspection to detect defects along with spectrometry to identify the material in the detect, in accordance with an embodiment of the present invention. As shown in FIG. 1, metrology device 100 includes a separate spectrometer path 110 and a darkfield path 120 to detect defects on the surface of a substrate 102 that is held on a stage 104. The darkfield path 120 is used to detect the presence of defects on the surface of the substrate 102, while the spectrometer path 110 is used to determine the type or material composition of the defect.

The metrology unit 100 includes a light source 112, which may be, e.g., a broadband light source that produces light with wavelengths between 190 and 800 nm, and an optical element that produces a line of illumination. The optical element may be, e.g., a lens 114, such as a cylindrical lens or lens system, that focuses the light from light source 112 in one direction and collimates the light in an orthogonal direction to produce the line of illumination that is incident on the substrate 102. If desired, the reflective optics may be used as the optical element to produce the line of illumination.

Figure 2:
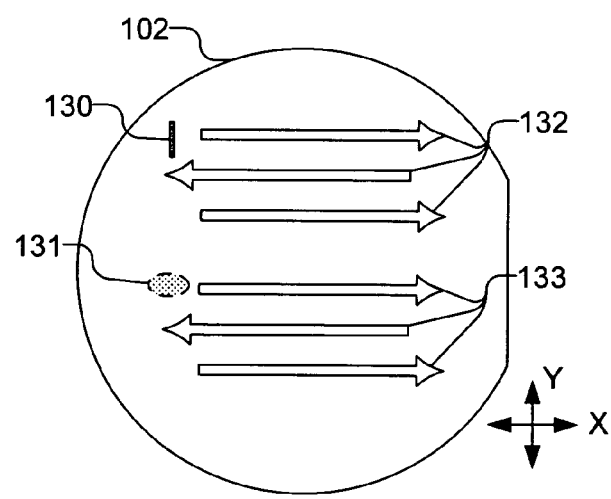
FIG. 2 illustrates a top view of a substrate with an illumination line that is produced by the metrology device.

FIG. 2 illustrates a top view of a substrate 102 with an illumination line 130 that is produced by lens 114. The illumination line 130 may be, e.g., 1 mm or larger in length and between 5 μm to 15 μm wide. The resolution is improved, however, with a narrow line, and thus, the illumination line 130 is preferably less than 5 μm wide, e.g., 1 μm to 5 μm or less. In operation, the substrate 102 or the metrology device 100 (or a combination of the two) is moved to scan the illumination line 130 across the surface of the substrate 130. By way of example, the stage 104 may be movable in the Cartesian Coordinate (XY) system illustrated in FIG. 2. Alternatively, the stage 104 may move in Polar Coordinate (R-θ) system, however, it may be necessary to correct for rotational effects, such as remapping the density of an inner diameter of a scan compared to the outer diameter because of the difference in speed at the inner and outer diameters of the scans.

In one embodiment, instead of an illumination line 130, an area of illumination 131 (illustrated with broken lines in FIG. 2) may be used. In this embodiment, instead of using an optical element, such as cylindrical lens 114, that focuses the light in one direction and collimates the light in an orthogonal direction to form a line, another optical element that illuminates an area of the substrate would be used, e.g., collimating the light or projecting a field aperture on the substrate. The area of illumination 131 may be scanned across the surface of the substrate in a manner similar to that described above, as indicated by arrows 133 in FIG. 2.

In an XY coordinate system, the substrate 102 or the optics in the metrology device 100 (or a combination of the two) is moved to scan the illumination line 130 back and forth over the surface of the substrate 102, as illustrated by lines 132, such that the end of the illumination line 130 is adjacent to or slightly overlaps the area scanned in the previous pass. Alternatively, the illumination line 130 may be raster scanned over the surface of the substrate 102. The scanning of the substrate 102 continues until the desired area of the substrate 102 has been scanned.

As illustrated in FIG. 1, the light from light source 112 is incident on the substrate 102 at an oblique incidence. In the spectrometer path 110, a reflective or refractive optical element, illustrated as lens 116, which may be convex lens or lens system, focuses the illumination line that is spectrally reflected ($0^{th}$ order) by substrate 102 into a spot that is received by detector 118. The detector 118 may be, e.g., a spectrophotometer, with a lens or lens system 142 (or reflective elements) and a diffraction grating 144 that spreads the light from the sample 102 into its spectral components onto a detector array 146, such as a CCD or CMOS imaging sensor, the operation of which is well known.

If desired, the metrology unit 100 may use a spectral ellipsometer in the spectrometer path 110, including, e.g., a polarizer 115 and analyzer 117, illustrated with broken lines in FIG. 1. Thus, the metrology unit 100 may use both spectral information as well as polarimetry information. The polarizer 115 and analyzer 117 may be located before or after the lens elements 114 and 116 respectively and may be rotated to modulate the polarization intensity. It should be understood that other optical elements, such as a compensator, may be used.

Figure 3A:
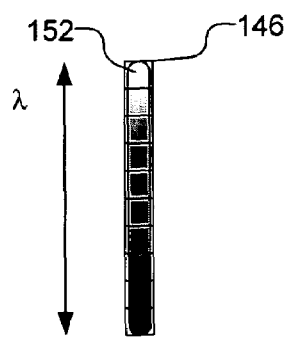
FIGS. 3A, 3B, and 3C illustrate top views of different embodiments of the detector used in the spectrally reflected light detector.

FIG. 3A illustrates one embodiment of the array 146 in detector 118. As illustrated in FIG. 3A, array 146 may be one dimensional. The reflected light from illumination line 130 is focused to a spot on the detector 118 and the spectral information, illustrated by band 152, is collected along the vertical axis, labeled λ, of the array 146. As the illumination line 130 is scanned across the surface of the substrate 102, the data from the array is periodically loaded or transferred and the array is refreshed. The refresh rate of the array 146 should be adequate to record the information from illumination line 130 without a loss of data, i.e., the array 146 should be refreshed when (or before) the illumination line 130 has traveled a full width's distance.

Figure 3B:
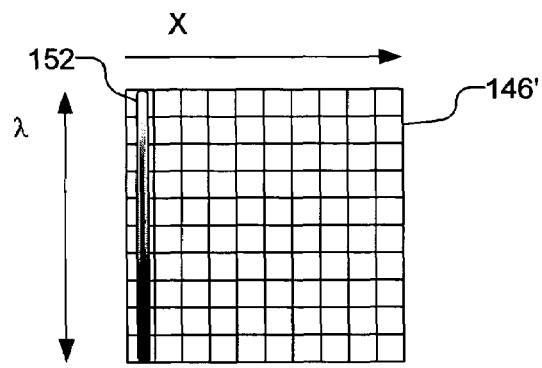

FIG. 3B illustrates a two dimensional array 146' that is another embodiment of the array in detector 118. The spectral information 152 from the reflected light from illumination line 130 is collected along the first column of pixels in the array 146' along the vertical axis labeled λ. As the illumination line 130 is scanned across the substrate 102, the collected spectral information 152 is transferred from one column to the next along the horizontal axis labeled λ and then read out of the array 146'. Alternatively, the spectral information 152 maybe scanned across the array 146' as the illumination line 130 is scanned across the substrate 102 and the data from the array 146' is transferred after each pass.

Figure 3C:
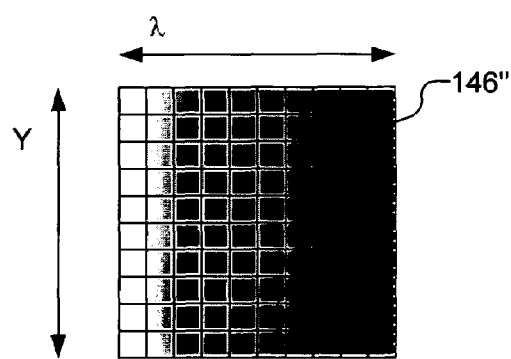

FIG. 3C illustrates another two dimensional array 146" that is another embodiment of the array in detector 118. In the present embodiment, instead of receiving a spot from lens 116 in FIG. 1, the detector 118 receives a line, e.g., lens 116 may be a cylindrical lens or lens system. The detector 118 spreads the light from the sample 102 into its spectral components onto a two dimensional detector array 146", which is illustrated shown in FIG. 3C. The length of the illumination line 130 is focused along one dimension of the array 146", e.g., the vertical axis label Y, while the spectral information is received along the horizontal axis, labeled λ. As discussed in reference to FIG. 3A, the data from the array 146" is periodically loaded or transferred and the array is refreshed while the illumination line 130 is scanned across the surface of the substrate 102. The refresh rate of the array 146" should be adequate to record the information from illumination line 130 without a loss of data, i.e., the array 146" should be refreshed when (or before) the illumination line 130 has traveled a full width's distance.

As illustrated in FIG. 1, the darkfield path 120 of the metrology device 100 may be positioned approximately normal to the surface of the substrate 102. A reflective or refractive optical element, illustrated as lens or lens system 122, focuses the darkfield image of the illumination line on the substrate 102 onto an image detector 124, such as a CCD or CMOS imaging sensor, the operation of which is well known. As is well known in the art, "darkfield" refers to a metrology technique in which a specimen, e.g., a defect, is illuminated from the side and light scattered from the specimen is detected, resulting in a dark background and a luminescent specimen.

Because the sample 102 may include diffractive elements that are not defects, the incident angle of the light from light source 112 may be varied, as indicated by arrow 113 in FIG. 1, to ensure that light diffracted from non-defect diffractive elements does not coincide with the darkfield path 120 and therefore interfere with the darkfield image. As the angle of incidence is varied, the position of the detector 118 may be correspondingly varied, as indicated by arrow 119, so that detector 118 receives the spectrally reflected ($0^{th}$ order). If desired, the angle of incidence may be held stationary and the position of the darkfield path 120, e.g., the image detector 124 and lens 122, may be varied to receive the darkfield image, as illustrated by broken arrow 121. Alternatively, a filter 125 may be used at the pupil plane of the imaging path of the detector 124 to block the first order light from the periodic structure on the substrate 102.

Figure 4A:
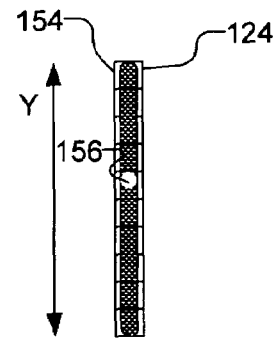
FIGS. 4A, 4B, and 4C illustrate top views of different embodiments of the image detector used in the darkfield detector.

FIG. 4A illustrates a top view of one embodiment of the image detector 124 used in the darkfield path 120 of the metrology device 100. The image detector 124 may be a one dimensional array that receives the length of the darkfield image from illumination line 130 along the axis labeled Y. The darkfield image 154 of the illumination line 130 is illustrated superimposed over the detector 124 with a defect 156 illustrated as a white spot in the darkfield image 152. Similar to array 146, described in reference to FIG. 3A, the data from the array 124 is periodically loaded or transferred and the array is refreshed as the illumination line 130 is scanned. The refresh rate of the array 124 should be adequate to record the information from illumination line 130 without a loss of data, i.e., the array 124 should be refreshed when (or before) the illumination line 130 has traveled a full width's distance.

Figure 4B:
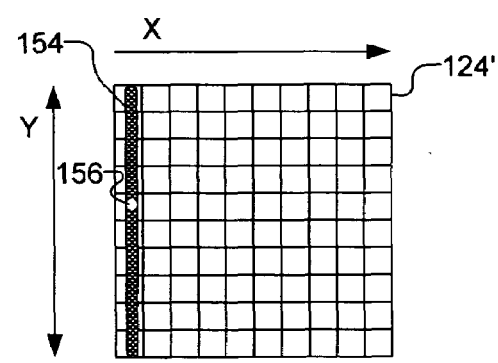

In another embodiment, illustrated in FIG. 4B, a two dimensional image array 124' is used. The darkfield image 154 from the illumination line may be imaged on the first column of pixels in the array 124', e.g., the length of the darkfield image 154 is imaged along the vertical axis labeled Y. As the illumination line 130 is scanned across the substrate 102, the collected darkfield image 154 is transferred from one column to the next along the horizontal axis labeled X and then read out of the array 124'. Alternatively, darkfield image 154 maybe scanned across the array 124' as the illumination line 130 is scanned across the substrate 102 and the data from the array 124' is transferred after each pass.

Figure 4C:
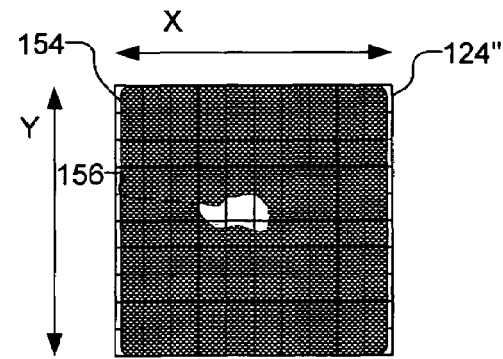

In another embodiment, illustrated in FIG. 4C, a two dimensional image array 124" is used and the darkfield image is projected over an area of the array 124". It should be understood that while the area of the array 124" that is covered by the darkfield is shown to be square in FIG. 4C, the darkfield image may have other geometric shapes. In this embodiment, instead of a using a line of illumination on the surface of the substrate, an area of illumination 131 is used, such as that shown in FIG. 2. The data from the array 124" is periodically loaded or transferred and the array is refreshed while the area of illumination is scanned across the surface of the substrate 102. The refresh rate of the array 124" should be adequate to record the information from area of illumination without a loss of data, i.e., the array 124" should be refreshed when (or before) the area of illumination has traveled a full width's distance. Alternatively, the image of the area of illumination is transferred from one column to the next synchronized with the scanning of the area of illumination across the substrate.

As shown in FIG. 1, the detectors 124 and 146 are coupled to a processor 160, which receives and processes the data from the detectors. Using the data from detector 124 in the darkfield path 120, the processor 160 can determine the size, geometry, and intensity of a defect on the substrate. Processing darkfield data to detect the presence of a defect is well known in the art. Additionally, when a defect is detected, the processor 160 can use the spectral data from detector 146 to identify the type and material composition of defect. For example, when the darkfield image indicates the presence of a defect, but the spectral information from the detector 146 indicates that the optical parameters, such as refractive index or absorption coefficient, does not change, the defect may be a scratch or other structural defect. On the other hand, if the spectral information indicates that one or more optical parameters change, the defect may be contamination, such as a foreign particle or fingerprint. The processor 160 may determine the composition of the defect using the spectral data using well known spectrometer and/or ellipsometer techniques. The composition of the foreign particle can then be used to identify the source of the defect.

The processor 160 may include a data structures and software code for automatically implementing the one or more acts described in this detailed description, which can be implemented by one of ordinary skill in the art in light of the present disclosure and stored on a computer readable storage medium. The storage medium may be any device or medium that can store code and/or data for use by a computer system such as computer 160 in FIG. 1. This includes, but is not limited to, magnetic and optical storage devices such as disk drives, magnetic tape, compact discs, and DVDs (digital versatile discs or digital video discs), and computer instruction signals embodied in a transmission medium (with or without a carrier wave upon which the signals are modulated.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A metrology device comprising:
    a stage for holding a substrate;
    a broadband light source that produces an illumination on a portion of the surface of the substrate at an oblique angle of incidence, wherein at least one of the stage and the broadband light source is movable to scan the illumination across the surface of the substrate;
    a first detector positioned to collect the darkfield image from the illumination;
    a second detector positioned to collect the spectrally reflected light from the surface of the substrate; and
    a processor coupled to the first detector and the second detector and that determines the presence of a defect on the surface of the substrate from the darkfield image and the material composition of defect from the spectrally reflected light.

2. The metrology device of claim 1, wherein the broadband light source produces an illumination line on the surface of the substrate, wherein the first detector collects the darkfield image from the illumination line.

3. The metrology device of claim 1, wherein the angle of incidence of the illumination is variable to produce a darkfield image on the first detector and the position of the second detector is variable to collect the spectrally reflected light.

4. The metrology device of claim 1, wherein the position of the first detector is variable to collect the darkfield image.

5. The metrology device of claim 1, further comprising a filter for the first detector, the filter filtering out light from a non-defect diffracting structure on the substrate.

6. The metrology device of claim 2, further comprising an optical element that collimates the beam of light in a first direction and focuses the beam of light in a second direction that is orthogonal to the first direction to produce the illumination line.

7. The metrology device of claim 6, wherein the optical element is a cylindrical lens element.

8. The metrology device of claim 1, wherein the first detector is positioned along a light path that is approximately normal to the surface of the substrate.

9. The metrology device of claim 1, wherein the stage is movable in at least one of Cartesian coordinates and polar coordinates.

10. The metrology device of claim 2, wherein the first detector is a one dimensional array of photodetecting elements.

11. The metrology device of claim 2, wherein the first detector is a two dimensional array of photodetecting elements, and wherein the illumination line has a length in a first direction and a width in a second direction, the darkfield image of the length of the illumination line is collected along a first dimension of the first detector, and the collected darkfield image is transferred along the second dimension as the illumination line is scanned across the surface of the substrate.

12. The metrology device of claim 1, wherein the first detector is a two dimensional array of photodetecting elements, and wherein the broadband light source produces an area of illumination on a portion of the surface of the substrate, the darkfield image of the area of illumination is collected on the two-dimensional array.

13. The metrology device of claim 1, wherein the second detector is a spectrophotometer and includes a one dimensional array of photodetecting elements, wherein the spectrum of the spectrally reflected light is collected along the one dimensional array.

14. The metrology device of claim 1, wherein the second detector is a spectrophotometer and includes a two dimensional array of photodetecting elements, wherein the spectrum of the spectrally reflected light is collected along a first dimension of the two dimensional array, and the collected spectrally reflected light is transferred along the second dimension of the two dimensional array as the illumination is scanned across the surface of the substrate.

15. The metrology device of claim 2, wherein the second detector is a spectrophotometer and includes a two dimensional array of photodetecting elements, and wherein the illumination line has a length in a first direction and a width in a second direction, the spectrum of the spectrally reflected light is collected along a first dimension of the two dimensional array, and the spectrally reflected light along the length of the illumination line is collected along the second dimension of the two dimensional array.

16. The metrology device of claim 1, further comprising a polarization state generator between the broadband light source and the substrate and a polarization state analyzer between the substrate and the second detector.

17. A method of detecting and identifying the material composition of defects on a substrate, the method comprising producing broadband light;
illuminating a portion of the surface of a substrate at an oblique angle of incidence with one of an illumination line and an area of illumination;
scanning the illumination across the surface of the substrate;
collecting the darkfield image from the illumination with a first detector as the illumination is scanned across the substrate;
collecting the spectrally reflected light from the surface of the substrate with a second detector as the illumination is scanned across the substrate;
determining the presence of a defect on the surface of the substrate using the collected darkfield image and the material composition of the defect using the collected spectrally reflected light; and
storing the determined presence of the defect and the material composition of the defect.

18. The method of claim 17, further comprising forming the broadband light into an illumination line on the surface of the substrate.

19. The method of claim 17, further comprising:
varying the angle of incidence of the illumination on the surface of the substrate until a darkfield image is formed at the first detector; and
varying the position of the second detector to collect the spectrally reflected light from the illumination.

20. The method of claim 17, further comprising varying the position of the first detector to collect the darkfield image.

21. The method of claim 17 further comprising filtering the light from a non-defect diffracting structure on the substrate before the first detector collects the darkfield image.

22. The method of claim 17, further comprising:
polarizing the illumination prior to the illumination line being incident on the surface of the substrate; and
analyzing the spectrally reflected light before being detected by the second detector.

23. The method of claim 17, wherein the illumination is scanned across the surface of the substrate by moving a stage that holds the substrate relative to the illumination.

24. The method of claim 23, wherein the stage moves in at least one of Cartesian coordinate and polar coordinates.

25. The method of claim 18, wherein the illumination line has a length in a first direction and a width in a second direction, and wherein the darkfield image of the length of the illumination line is collected along a first dimension of the first detector and the collected darkfield image is transferred along the second dimension as the illumination line is scanned across the surface of the substrate.

26. The method of claim 17, wherein the surface of a substrate is illuminated with an area of illumination, and wherein the darkfield image of the area of illumination is collected over an area of the first detector.

27. The method of claim 17, wherein the spectrum of the spectrally reflected light is collected along a first dimension of the second detector.

28. The method of claim 18, wherein the illumination line has a length in a first direction and a width in a second direction, the spectrum of the spectrally reflected light is collected along a first dimension of the second detector and the spectrally reflected light along the length of the illumination line is collected along a second dimension of the second detector.

29. An apparatus comprising:
a stage for holding a substrate;
a metrology device for detecting and identifying defects on the substrate on the stage, wherein at least one of the stage and the metrology unit is movable with respect to the other to produce relative movement between the substrate held on the stage and the metrology unit, the metrology unit comprising:
a variable angle light source that produces a polychromatic beam of light to be incident on the substrate held on the stage at an oblique angle;
at least one optical element that produces an illumination line on the substrate held on the stage, the illumination line having a length and a width, the at least one optical element collimates the beam of light in a first direction and focuses the beam of light in a second direction that is orthogonal to the first direction;
a first detector that collects a darkfield image from the illumination line on the substrate held on the stage, the first detector having an array of photodetecting elements, wherein the darkfield image of the length of the illumination line is collected along a first dimension of the first detector during the relative movement between the substrate held on a stage and the metrology unit;
a variable angle second detector that collects the spectrally reflected light from the substrate held on the stage, the second detector having an array of photodetecting elements, wherein the spectrum of the spectrally reflected light is collected along a first dimension of the array of photodetecting elements during the relative movement between the substrate held on a stage and the metrology unit; and
a processor coupled to receive data from the first detector and data from the variable angle second detector and that determines the presence of a defect on the substrate from the data provided by the first detector and the material composition of the defect from the data provided by the variable angle second detector.

30. The apparatus of claim 29, wherein the spectrally reflected light along the length of the illumination line is collected along a second dimension of the variable angle second detector.

31. The apparatus of claim 29, wherein the darkfield image of the width of the illumination line is collected along a second dimension of the first detector.

32. The apparatus of claim 29, wherein the first detector is positioned along a path that is approximately normal to a surface of the substrate held on the stage.

* * * * *